United States Patent [19]
Barker et al.

[11] Patent Number: 5,861,224
[45] Date of Patent: Jan. 19, 1999

[54] ELECTROLYTE SOLVENT FOR LITHIUM ION ELECTROCHEMICAL CELL

[75] Inventors: Jeremy Barker; Feng Gao, both of Henderson, Nev.

[73] Assignee: Valence Technology, Inc., Henderson, Nev.

[21] Appl. No.: 893,068

[22] Filed: Jul. 15, 1997

[51] Int. Cl.$^6$ .................................................. H01M 10/40
[52] U.S. Cl. ........................... 429/194; 429/192; 429/197
[58] Field of Search .................................... 429/194, 197, 429/192

[56] References Cited

U.S. PATENT DOCUMENTS

| | | | |
|---|---|---|---|
| 5,013,620 | 5/1991 | Miyazaki et al. | 429/194 |
| 5,206,408 | 4/1993 | Liotta, Jr. | 558/277 |
| 5,206,409 | 4/1993 | Romano et al. | 558/277 |
| 5,451,477 | 9/1995 | Omaru et al. | 429/218 |
| 5,521,027 | 5/1996 | Okuno et al. | 429/194 |
| 5,534,649 | 7/1996 | Cho et al. | 558/277 |
| 5,633,099 | 5/1997 | Yokoyama et al. | 429/197 |

FOREIGN PATENT DOCUMENTS

| | | |
|---|---|---|
| 06290809 | 10/1994 | Japan . |
| 07/326385 H | 12/1995 | Japan . |
| 08/096847 A | 4/1996 | Japan . |

OTHER PUBLICATIONS

*Comprehensive Organic Functional Group Transformations*, Katrisky, A.R. et al., Ed. in Chief, vol. 6, Gilchrist Ed. (pp. 460–461) 1995, *Synthesis: Carbon with Three or Four Attached Heteroatoms*, Pergamon. No month available.

*Primary Examiner*—Stephen Kalafut
*Assistant Examiner*—Carol Chaney
*Attorney, Agent, or Firm*—Robert Krebs

[57] ABSTRACT

Non-aqueous solid electrochemical cells with improved performance can be fabricated by employing an electrolyte having an electrolyte solvent which contains a carbonate having the structure R'OCOOR" where R' and R" are independently selected from branched alkyl groups with 3 to 7 carbons. A preferred solvent includes diisopropyl carbonate. The cells are particularly suited for low and high temperature applications.

26 Claims, No Drawings

ELECTROLYTE SOLVENT FOR LITHIUM ION ELECTROCHEMICAL CELL

FIELD OF THE INVENTION

The present invention relates to electrochemical devices and, more particularly, to non-aqueous electrochemical cells demonstrating improved performance. In particular, the electrochemical cell includes an anode comprising graphite or coke as the intercalation material and an electrolyte solvent comprising a carbonate having the structure R'OCOOR" where R' and R" are independently selected from branched alkyl groups with 3 to 7 carbons.

BACKGROUND OF THE INVENTION

Non-aqueous lithium electrochemical cells typically include an anode, a lithium electrolyte prepared from a lithium salt dissolved in one or more organic solvents and a cathode of an electrochemically active material, typically a chalcogenide of a transition metal. During discharge, lithium ions from the anode pass through the liquid electrolyte to the electrochemically active material of the cathode where the ions are taken up with the simultaneous release of electrical energy. During charging, the flow of ions is reversed so that lithium ions pass from the electrochemically active cathode material through the electrolyte and are plated back onto the lithium anode. Non-aqueous lithium electrochemical cells are discussed in U.S. Pat. Nos. 4,472,487, 4,668,595, 5,028,500, 5,441,830, 5,460,904, and 5,540,741.

Recently, the lithium metal anode has been replaced with a carbon anode such as coke or graphite intercalated with lithium ions to form $Li_xC$. In operation of the cell, lithium passes from the carbon through the electrolyte to the cathode where it is taken up just as in a cell with a metallic lithium anode. During recharge, the lithium is transferred back to the anode where it reintercalates into the carbon. Because no metallic lithium is present in the cell, melting of the anode does not occur even under abuse conditions. Also, because lithium is reincorporated into the anode by intercalation rather than by plating, dendritic and spongy lithium growth does not occur.

Various factors influence the performance of electrochemical cells. For instance, electrolyte decomposition will occur with any solvent at high enough potential. In the case of lithium cells, the solvents are organic, aprotic, polar solvents. Conventional solvents are described, for example, in U.S. Pat. Nos. 5,085,952, 4,925,751, 4,908,283, 4,830,939, and 4,792,504. Decomposition of solvents occurs at different rates and at different potentials. In the case of conventional exemplary carbonates, the solvent may be a cyclic carbonate or linear carbonate, yet the same decomposition mechanism applies at different rates. Exemplary organic solvents are γ-butryrolactone, tetrahydrofuran, propylene carbonate, vinylene carbonate, ethylene carbonate, dimethyl carbonate (DMC), diethyl carbonate (DEC), butylene carbonate, methyl ethyl carbonate, dipropyl carbonate, dibutyl carbonate, diethoxy ethane, dimethoxyethane, and dioxolane.

Loss of performance due to impurities and undesired side reactions has lead to the selection of solvents and salts which are less reactive with cell components. Unfortunately, this eliminates from use certain solvents and salts which perform better in a cell as compared to their less reactive counterparts. Therefore, what is needed is an understanding of the mechanisms causing undesirable loss of performance and reduce battery life cycle. Although interaction with metallic lithium has now been resolved by eliminating the use of the metallic lithium, yet there still remains the challenge of determining how to prevent undesired side reactions especially those involving formation of gas in cells.

SUMMARY OF THE INVENTION

The present invention is based in part on the discovery that the use of a carbonate having the structure R'OCOOR" where R' and R" are independently selected from branched alkyl groups with 3 to 7 carbons and, in particular, diisopropyl carbonate in lithium ion electrochemical cells employing carbon anodes provides for cells wherein the electrolyte solvent remains stable and does not decompose appreciably, even at high temperatures. The cells are also suited for low temperature applications. It has been found that if a graphite negative electrode (anode) is used in an electrolyte containing various carbonates as the solvent, the solvent is apparently absorbed into the active sites of the graphite negative electrode and readily generates gas through decomposition. As a result, the decomposition of the solvent prevents lithium ion as an active material from intercalating into the graphite on charging the battery and causes an increase in polarization; consequently, the battery capacity is decreased. Such decomposition of the carbonates results in the evolution of the gas, probably methane, ethylene, and/or ethane.

The inventive electrolyte solvent is expected to overcome the problems associated with prior solvents and to simultaneously fulfill the requirements of high reactivity, good charge rate capabilities, acceptable life cycle, specific rate and stability. In addition, electrochemical cells will have a first cycle capacity loss of only about 10% to 35%, where the first cycle discharge loss (%) =

$$\frac{(\text{first cycle charge capacity} - \text{first cycle discharge capacity}) \times 100}{\text{first cycle charge capacity}}$$

In one aspect, the invention is directed to an electrochemical cell that includes:

an anode comprising a carbon active material comprising graphite, coke, or mixture thereof and a binder;
a cathode; and
an electrolyte, that is interposed between the anode and cathode, that comprises a salt and a solvent comprising a carbonate having the structure R'OCOOR" where R' and R" are independently selected from branched alkyl groups with 3 to 7 carbons.

In another aspect, the invention is directed to a method of fabricating an electrochemical cell that includes the steps of:

(a) providing an anode comprising a carbon active material comprising graphite, coke, and mixtures thereof and a binder;
(b) providing a cathode; and
(c) forming an electrolyte containing a salt and a solvent that is interposed between said anode and said cathode wherein the solvent comprises a carbonate having the structure R'OCOOR" where R' and R" are independently selected from branched alkyl groups with 3 to 7 carbons.

Preferably the carbonate is symmetrical. A preferred carbonate is diisopropyl carbonate.

A feature of the invention is that the electrochemical cells is expected to operate at low temperatures below −30° C. The present invention provides a novel electrolyte solvent and method for preventing decomposition of one or more electrochemical components and for preventing undesired gaseous by-products resulting from the decomposition which may lead to volumetric expansion of an electrochemical cell and possible rupture. The novel electrolyte solvent is usable with a variety of carbonaceous and metal oxide electrode active materials, providing improved performance with less decomposition and gas formation which occur with other solvents. The invention provides an electrolyte stabilized against decomposition during cyclic operation of an electrochemical cell. The electrolyte includes a specifically selected class of new solvents which are resistant to decomposition and formation of gaseous by-products resulting from decomposition. The new solvents, when used as co-solvents, stabilize other solvents in the solvent mixture.

DETAILED DESCRIPTION OF THE PREFERRED EMBODIMENTS OF THE INVENTION

As noted above, this invention is directed to non-aqueous electrochemical cells which by virtue of the solvent employed provide for enhanced electrochemical performance even at extreme temperatures as low as about −30° C. and as high as about 90° C. The present invention provides an electrochemical cell or battery which has virtually no gassing or a very low rate of gassing as compared to conventional cells and batteries using conventional electrolyte solvents. Advantageously, the solvent of the present invention exhibits good performance even with carbonaceous electrode active materials and with transitional metal electrode active materials which show poor performance when used with conventional organic solvents. Preferred electrochemical cells contain an electrolyte that comprises a separator layer (e.g., polymer matrix layer) and an electrolyte solution.

However, prior to describing the invention in further detailed, the following terms will be defined.

The term "plasticizer" refers to an organic solvent, with limited solubility of polymers, that facilitates the formation of porous polymeric structures. By "porous structure" is meant that upon extraction of the plasticizer the polymer remains as a porous mass. Suitable plasticizers have high boiling points typically from about 100° C. to about 350° C. A number of criteria are important in the choice of plasticizer including compatibility with the components of the electrochemical cell precursor, processability, low polymer solubility and extractability liquid solvents (e.g., diethyl ether) or by supercritical fluids for example. Preferred plasticizers include, for example, dibutyl phthalate, dioctylphthalate, and acetates, glymes, and low molecular weight polymers.

In operation, for fabricating a solid polymeric matrix and composite electrode that includes polymeric binders, for example, the plasticizer is first well mixed with a polymer. Thereafter the plasticizer is removed by extraction and in the process the porous structure is formed. Preferably the weight ratio of plasticizer to polymer is from about 1 to about 50, more preferably about 10 to about 30, and most preferably about 20 to about 25.

The term "electrochemical cell precursor" or "electrolytic cell precursor" refers to the structure of the electrochemical cell prior to the addition of the inorganic salt and electrolyte solution. The precursor typically comprises (each in precursor form) an anode, a cathode, and solid polymeric matrix. The anode and/or cathode may each include a current collector. For a liquid electrolytic cell, a separator made of any suitable material such as, for example, glass fiber, polyethylene, or polypropylene is employed instead of a solid polymeric matrix.

The term "activation" refers to the placement of an electrolyte solution into the porous portions of an electrochemical cell precursor. After activation, the electrochemical cell is charged by an external energy source prior to use.

The term "electrolytic cell" or "electrochemical cell" refers to a composite containing an anode, a cathode and an ion-conducting electrolyte interposed therebetween.

The term "battery" refers to two or more electrochemical cells electrically interconnected in an appropriate series/parallel arrangement to provide the required operating voltage and current levels.

The term "solid polymeric matrix" refers to an electrolyte compatible material formed by polymerizing an organic or inorganic monomer (or partial polymer thereof) and which, when used in combination with the other components of the electrolyte, renders the electrolyte solid. Suitable solid polymeric matrices are well known in the art and include solid matrices formed from organic polymers, inorganic polymers or a mixture of organic polymers with inorganic non-polymeric materials. Preferably, the solid polymeric matrix is an organic matrix derived from a solid matrix forming monomer and from partial polymers of a solid matrix forming monomer. See, for example, U.S. Pat. Nos. 5,501,921, 5,498,491, 5,491,039, 5,489,491, 5,482,795, 5,463,179, 5,419,984, 5,393,621, 5,358,620, 5,262,253, 5,346,787, 5,340,669, 5,300,375, 5,294,501, 5,262,253, and 4,908,283, which are incorporated herein. Inorganic monomers are disclosed in U.S. Pat. Nos. 4,247,499, 4,388,385, 4,414,607, 4,394,280, 4,432,891, 4,539,276, and 4,557,985, which are incorporated herein.

The solid matrix forming monomer or partial polymer can be cured or further cured prior to or after addition of the salt, solvent and, optionally, a viscosifier. For example, a composition comprising requisite amounts of the monomer or partial polymer, salt, organic carbonate solvent and viscosifier can be applied to a substrate and then cured. Alternatively, the monomer or partial polymer can be first cured and then dissolved in a suitable volatile solvent. Requisite amounts of the salt, organic carbonate solvent and viscosifier can then be added. The mixture is then placed on a substrate and removal of the volatile solvent would result in the formation of a solid electrolyte. In either case, the resulting solid electrolyte would be a homogeneous, single phase product which is maintained upon curing, and does not readily separate upon cooling to temperatures below room temperature.

The term "substrate" refers to any suitable film made of material that is compatible with the components of the polymer mixture. The substrate serves as the vehicle or base onto which the electrode mixture is applied. After the solvent has evaporated from the mixture, the polymer matrix is formed. Suitable substrates include, for example, paper, e.g, 20 or 24 weight paper, polyester (MYLAR™), polypropylene, polyethylene films and non-woven webs.

Preferably, the solid polymeric matrix is formed by a casting process which does not require the use of monomers or prepolymers, that is, no curing is required. A preferred method employs a copolymer of vinylidenedifluroide and hexafluoropropylene dissolved in acetone or other suitable solvent(s). Upon casting the solution, the solvent is evaporated to form the solid polymeric matrix. The solution may be casted directly onto a current collector. Alternatively, the solution is casted onto a substrate, such as a carrier web, and after the solvent (e.g., acetone) is removed, an electrode film is formed thereon.

The term "salt" refers to any salt, for example, an inorganic salt, which is suitable for use in a non-aqueous electrolyte. Representative examples of suitable inorganic ion salts are alkali metal salts of less mobile anions of weak bases having a large anionic radius. Examples of such anions are $I^-$, $Br^-$, $SCN^-$, $ClO_4^-$, , $BF_4^-$, $PF_6^-$, $AsF_6^-$, $CF_3COO^-$, $CF_3SO_3^-$, $N(SO_2CF_3)_2^-$, and the like. Specific examples of suitable inorganic ion salts include $LiClO_4$, $LiSCN$, $LiBF_4$, $LiAsF_6$, $LiCF_3SO_3$, $LiPF_6$, $(CF_3SO_2)_2NLi$, $(CF_3SO_2)_3CLi$, NaSCN, and the like. The inorganic ion salt preferably contains at least one cation selected from the group consisting of Li, Na, Cs, Rb, Ag, Cu, Mg and K.

The electrolyte typically comprises from about 5 to about 25 weight percent of the inorganic ion salt based on the total weight of the electrolyte; preferably, from about 10% to 20%, and even more preferably from about 10% to about 15%. The percentage of salt depends on the type of salt and electrolyte solvent employed.

The electrolyte of the invention comprises a solvent(s) or solvent mixtures thereof. The solvents of the invention are generally characterized as non-linear carbonates with lower melting points and higher boiling points compared to the range observed for commonly used solvent such as dimethyl carbonate (DMC) which is a linear, non-branched carbonate. DMC does not have a high boiling point and is not suitable for high temperature operations. It is also not suitable for low temperature operations due to its high melting point. Solvents of the present invention preferably have melting point(s) of less than about $-30°$ C.

The non-linear carbonates of the invention are characterized by having further lower melting points and higher boiling points which render them useful as both high and low temperature solvents. The advantages of temperature spread between the melting point and the boiling point is achieved by the carbonates of the invention by employing non-linear alkyl groups which results in achieving advantages of broad temperature spread without significantly raising the viscosity.

The compounds usable as solvents according to the invention are carbonates of the general formula R'OCOOR" where R' and R" are each a non-linear, branched alkyl group having 3 to 7 carbons, and preferably 3 to 5 carbons. R' and R" are preferably the same to form a symmetric, acyclic, non-linear, branched carbonate. It is preferred that the solvent provides a viscosity of less than 0.90 cp at 25° C. Desirably, R' and R" are independently selected from the group consisting of isopropyl (i-propyl), tert-butyl (t-butyl), isobutyl (i-butyl), sec-butyl (s-butyl), tert-amyl (t-amyl), isoamyl (i-amyl), and neoamyl. The amyl compound may be any acyclic amyl. The term "amyl" refers to $C_5H_{11}$ group known to be present in several isomer forms. A preferred carbonate is isopropyl carbonate. The R' and R" groups each may themselves contain a substituent, therefore, each can be a non-linear alkyl or derivative thereof. The derivatives are formed by substitution which is selected to maintain a solidifying point (melting point) lower than that of dimethyl carbonate (DMC), that is, lower than about 5° C. Such derivatives are also characterized by resistance to decomposition, as compared to DMC. Other derivatives may be replacing a hydrogen with a substituent, in the alkyl hydrocarbon.

The carbonate compound of the invention may be used as a sole solvent or may be included in a solvent mixture. Such solvent mixture preferably includes one or more other organic solvents having a boiling point of about 80° C. to about 300 ° C. and where such other solvent is capable of forming a solute with lithium salts. Preferably such one or more other organic solvents is selected from the group, for example, ethylene carbonate (EC), dimethyl carbonate (DMC), diethyl carbonate (DEC), dipropyl ethane (DEE), ethyl methyl carbonate (EMC), butylene carbonate (BC), γ-butryrolactone, tetrahydrofuran, propylene carbonate, vinylene carbonate, dimethoxyethane, and dioxolane, and mixtures thereof. These carbonate solvents are commercially available. Even a small amount of the carbonate compound solvent of the invention is helpful to the mixture, therefore, the lower limit is greater than zero. A practical range by weight is 1:9 to 9:1 carbonate compound solvent to other organic solvent(s).

The general method for synthesizing the carbonates is illustrated by an exemplary reaction based on an alkyl haloformate and an organic alcohol. The reaction may be conducted at elevated temperature (50° C. to 80° C.) or at low temperature in the presence of an organic base, such as an amine or pyridine. Alternatively, the reaction may be conducted using an inorganic base. Starting with isopropyl chloroformate and isopropyl alcohol, DIPC can be made. As shown, the alkyl haloformate is isopropyl chloroformate. The chlorine leaving group is replace by the R" group of the isopropyl alcohol forming the exemplary DIPC. Alternatively, DIPC can be made in one step starting with isopropyl alcohol and phosgene. It is preferred that the symmetric branched carbonate be synthesized through the one step reaction using alcohol and the phosgene in a 2:1 ratio.

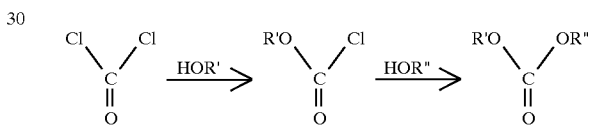

Where R' and R" are isopropyl alcohol, diisopropyl carbonate is formed.

Related processes are described in U.S. Pat. Nos. 5,206,408, 5,206,408, 5,534,649, and 5,563,288, each of which are incorporated herein. U.S. Pat. No. 5,206,408 describes a method to convert symmetric dialkyl carbonate, such as DMC, to an unsymmetric linear dialkyl carbonate by reacting the linear symmetric dialkyl carbonate with an alcohol selected from the group of alcohols containing the substituent for which substitution is desired. An example is methyl, butyl carbonate, made by substituting one of the methyl groups in the starting dialkyl, dimethyl carbonate. U.S. Pat. No. 5,206,409 describes a method to prepare a symmetric linear dialkyl carbonate, such as dimethyl carbonate. This dimethyl carbonate forms the precursor of the process of forming unsymmetric dialkyl carbonate as described in U.S. Pat. No. 5,206,408. U.S. Pat. No. 5,534,649 also describes a method for preparing symmetric dialkyl carbonates. The examples given are formation of dimethyl carbonate and diethyl carbonate by reaction of urea, methyl carbamate, ethyl carbamate with methanol and/or ethanol in the presence of a catalyst. U.S. Pat. No. 5,563,288 shows a method of making methyl isopropyl carbonate (MIPC) for use as an intermediate in forming di-(tertiary amino alkyl) carbonate.

The term "viscosifier" refers to a suitable viscosifier for solid electrolytes. Viscosifiers include conventional viscosifiers such as those known to one of ordinary skill in the art. Suitable viscosifiers include film forming agents well known in the art which include, by way of example, polyethylene oxide, polypropylene oxide, copolymers thereof, and the like, having a number average molecular weight of at least about 100 k, polyvinylpyrrolidone, carboxymethylcellulose, and the like. Preferably, the viscosifier is employed in an amount of about 1 to about 10 weight percent and more preferably at about 2.5 weight percent based on the total weight of the electrolyte composition.

The anode typically comprises a compatible anodic material which is any material which functions as an anode in a solid electrolytic cell. Such compatible anodic materials are well known in the art and include, by way of example, lithium, lithium alloys, such as alloys of lithium with aluminum, mercury, manganese, iron, zinc, intercalation based anodes such as those lithium intercalation anodes employing carbon materials such as graphite, cokes, mesocarbons, and the like. The carbon intercalation based anode precursors typically include a polymeric binder and extractable plasticizer suitable for forming a bound porous composite having a molecular weight of from about 1 k to 5,000 k. Examples of suitable polymeric binders include EPDM (ethylene propylene diamine termonomer), PVDF (polyvinylidene difluoride), HFP (hexafluoropropylene), EAA (ethylene acrylic acid copolymer), EVA (ethylene vinyl acetate copolymer), EAA/EVA copolymers, and copolymers of PVDF and HFP and the like. In one preferred embodiment, the carbon intercalation anode precursor (that is, the anode structure prior extraction) comprises from about 40 to about 70 weight percent of a carbon material (e.g., graphite); from about 8 to about 20 weight percent of a polymeric binder; and from about 15 to about 40 weight percent plasticizer. The anode may also include an electron conducting material such as carbon black.

For the present invention, the anode active material preferably comprises graphite or coke. While both natural and synthetic graphites may be employed, synthetic graphites that are highly structured, highly crystalline, anisotropic graphites having a nearly perfect layered structure are preferred. They are preferably formed by heat treatment up to about 3000° C. Examples are the SFG™ and KS™ series of synthetic graphites from Lonza G. & T., Limited (Sins, Switzerland). A preferred natural graphite is BG 35™ from Superior Graphite Co., Chicago, Ill. Although other anode materials may be used in addition to graphite or coke, in preferred embodiments, the anode active material consists essentially of graphite, coke, or a mixture thereof. Preferred cokes include, for example, those available as MCMB 2510™ from Osaka Gas Co., Japan and MGC™ from Mitsubishi Gas Co., Japan.

Electrochemical cells employing an anode comprising carbon active and an electrolytic solvent comprising the inventive solvent comprising diisopropyl carbonate, for example, are expected to maintain a high reversible specific capacity and demonstrate minimal first cycle capacity loss. Specifically, the electrochemical cell or battery is expected to exhibit a first cycle capacity loss of less than about 15% and which will be characterized by an anode having a reversible capacity of greater than about 316 milliamp hours per gram (mAh/g).

The cathode typically comprises a cathodic material or cathode active material (i.e., insertion compound) which is any material which functions as a positive pole in a solid electrolytic cell. Such cathodic materials are well known in the art and include, by way of example, transition metal oxides, sulfides, and selenides, including lithiated compounds thereof. Representative cathodic materials include cobalt oxides, manganese oxides, molybdenum oxides, vanadium oxides, sulfides of titanium, molybdenum and niobium, the various chromium oxides, copper oxides, lithiated cobalt oxides, e.g., $LiCoO_2$ and $LiCoVO_4$, lithiated manganese oxides, e.g., $LiMn_2O_4$, lithiated nickel oxides, e.g., $LiNiO_2$ and $LiNiVO_4$, and mixtures thereof. Cathode-active material blends of $Li_xMn_2O_4$ (spinel) is described in U.S. Pat. No. 5,429,890 which is incorporated herein. The blends can include $Li_xMn_2O_4$ (spinel) and at least one lithiated metal oxide selected from $Li_xNiO_2$ and $Li_xCoO_2$ wherein $0<x\leq2$. Blends can also include $Li_y$-$\alpha$-$MnO_2$ ($0\leq y<1$) which has a hollandite-type structure and is described in U.S. Pat. No. 5,561,007 which is incorporated herein.

In one preferred embodiment, the cathodic material is mixed with an electroconductive material including, by way of example, graphite, powdered carbon, powdered nickel, metal particles, conductive polymers (i.e., characterized by a conjugated network of double bonds like polypyrrole and polyacetylene), and the like, and a polymeric binder to form under pressure a positive cathodic plate. Suitable binders for use in the cathode have a molecular weight of from about 1 k to 5,000 k.

In one preferred embodiment, the cathode is prepared from a cathode paste which comprises from about 35 to 65 weight percent of a compatible cathodic material; from about 1 to 20 weight percent of an electroconductive agent; from about 1 to 20 weight percent of suitable polymeric binders that may include EPDM (ethylene propylene diene termonomer), PVDF (polyvinylidene difluoride), EAA (ethylene acrylic acid copolymer), EVA (ethylene vinyl acetate copolymer), EAA/EVA copolymers, copolymers of PVDF and HFP, and the like; from about 0 to about 20 weight percent of polyethylene oxide having a number average molecular weight of at least 100,000; from about 10 to 50 weight percent of electrolyte solvent; and from about 5 weight percent to about 25 weight of a solid matrix forming monomer or partial polymer thereof. Also included is an ion conducting amount of an inorganic ion salt. Generally, the amount of the salt is from about 1 to about 25 weight percent. (All weight percents are based on the total weight of the cathode.)

The electrolyte composition typically comprises from about 5 to about 25 weight percent of the inorganic ion salt based on the total weight of the electrolyte; preferably, from about 10 to 20 weight percent; and even more preferably from about 10 to about 15 weight percent. The percentage of salt depends on the type of salt and electrolytic solvent employed.

The electrolyte composition typically comprises from 0 to about 80 weight percent electrolyte solvent based on the total weight of the electrolyte; preferably from about 60 to about 80 weight percent; and even more preferably about 70 weight percent.

The electrolyte composition typically comprises from about 5 to about 30 weight percent of the solid polymeric matrix based on the total weight of the electrolyte; preferably from about 15 to about 25 weight percent.

In a preferred embodiment, the electrolyte composition further comprises a small amount of a film forming agent. Suitable film forming agents are well known in the art and include, by way of example, polyethylene oxide, polypropylene oxide, copolymers thereof, and the like, having a numbered average molecular weight of at least about 100 k. Preferably, the film forming agent is employed in an amount of about 1 to about 10 weight percent and more preferably at about 2.5 weight percent based on the total weight of the electrolyte composition.

METHODOLOGY

Methods of fabricating electrochemical cells are known in the art. See, for example, U.S. Pat. Nos. 5,300,373, 5,316, 556, 5,346,385, 5,262,253, 4,472,487, 4,668,595, and 5,028, 500, all of which are incorporated herein. The following illustrates a method of how an electrolytic cell could be fabricated with using the inventive electrolyte solvent mixtures. Examples 1 and 2 describe the process of preparing the anode and cathode, respectively. Example 3 describes the procedures for assembly a solid electrolytic cell.

The anode generally comprises an anode film that is laminated onto one or both sides of the current collector which is a thin metal foil or grid. Typically, each anode film is from about 100 $\mu$m to about 250 $\mu$m in thickness, preferably about 110 $\mu$m to about 200 $\mu$m, and more preferably about 125 $\mu$m to about 175 $\mu$m Similarly, the cathode of the present invention generally comprises a cathode film that is laminated onto one or both sides of the cathode current collector which is a thin metal foil or grid. Typically, each cathode film is from about 100 $\mu$m to about 200 $\mu$m in thickness, preferably about 130 $\mu$m to about 175 $\mu$m, and more preferably about 140 $\mu$m to about 165 $\mu$m.

Current collectors for the anode and cathode can comprise, for example, a screen, grid, expanded metal, woven or non-woven or knitted wire fabric formed from an electron conductive material such as metals or alloys. Preferably, the current collector has a thickness from about 25 $\mu$m to about 75 $\mu$m, preferably about 35 $\mu$m to about 65 $\mu$m, and more preferably about 45 $\mu$m to about 55 $\mu$m. Each current collector is also connected to a current collector tab which extends from the edge of the current collector. In batteries comprising multiple electrochemical cells, the anode tabs are preferably welded together and connected to a nickel lead. The cathode tabs are similarly welded and connected to a lead. External loads can be electrically connected to the leads. Current collectors and tabs are described in U.S. Pat. No. 4,925,752, 5,011,501, and 5,326,653, which are incorporated herein.

The invention will be described using the anode and cathode structures wherein electrode materials (or films) are laminated onto both sides of the current collectors, however, it is understood that the invention is applicable to other configurations, for example, where one side of the anode and/or cathode current collector is laminated.

EXAMPLE 1

The anode current collector employed was a sheet of expanded copper metal that is about 50 $\mu$m thick. It is available under the designation 2Cu5-125 (flatten) from Delker Corp., Branford, Conn. The anode slurry was prepared as follows:

A polymer mixture comprising a copolymer of vinylidenedifluoride VDF and hexafluoropropylene (HFP) was prepared by mixing 6.8 grams of the copolymer in 20 grams of acetone. The copolymer (ave. MW 125K) was Kynar Flex 2801™ from Elf Atochem North America, in Philadelphia, Pa. The mixture was stirred for about 24 hours in a milling jar available from VWR Scientific, in San Francisco, Calif., model H-04172-00. The copolymer functions as a binder for the carbon in the anode.

A graphite mixture was prepared separately by first adding 23.4 grams of BG 35™ graphite (Superior Graphite Co.) into a solution containing 60 grams acetone, and 10.5 grams dibutyl phthalate. The graphite was vigorously mixed in a high shear mixer until a substantially homogeneous blend was formed. A suitable mixer is available from Ross Model ME100DLX, Hauppauge, N.Y., operating at its highest setting (about 10,000 RPM) for 30 minutes.

The anode slurry was prepared by mixing the polymer mixture and the graphite mixture together under low shear conditions to form the anode slurry wherein the components are well mixed. A portion of the acetone is allowed to evaporate from the slurry before it was laminated onto each side of the current collector. Anode films form when the remaining portion of the acetone evaporates.

EXAMPLE 2

The cathode current collector employed was a sheet of expanded aluminum that is about 50 $\mu$m thick. The aluminum grid is available under the designation 2AL5-077 from Delker Corp. The cathode slurry was prepared as follows:

A polymer mixture comprising a copolymer of vinylidenedifluoride VDF and hexafluoropropylene (HFP) was prepared by mixing 4.4 grams of the copolymer in 15 ml of acetone. The copolymer was Kynar Flex 2801™. The mixture was stirred for about 24 hours in a milling jar.

A cathode mixture was prepared separately by mixing 28.9 grams of $LiMn_2O_4$, 2.4 grams of carbon black (Super P™) into a solution containing 60 grams acetone, and 8.7 grams dibutyl phthalate. The mixture was then vigorously mixed in the a high shear mixer until a substantially homogeneous blend was formed. As further described below, the amount of cathode-active material $LiMn_2O_4$ employed can be varied to provide different cathode to anode mass ratios.

The cathode slurry was prepared by mixing the polymer mixture and the cathode mixture together under low shear conditions to form the cathode slurry wherein the components are well mixed. A portion of the acetone is allowed to evaporate from the slurry before it was laminated onto each side of the current collector. Cathode films form when the remaining portion of the acetone evaporates.

The above anode and cathode films were formed directly on the current collector by laminating the slurry mixtures onto the current collector surfaces. Alternatively, each film can be prepared by first casting a slurry onto a substrate or carrier web and allowing the solvent to evaporate thus leaving the film. Thereafter, the films can be laminated onto each side of the current collector.

EXAMPLE 3

A solid electrochemical cell is prepared by first positioning a polymeric matrix between the anode and cathode and thereafter fusing the structures under moderate pressure and temperature (e.g., 130° C.) to form an electrochemical cell precursor. The polymeric matrix is formed by casting a polymeric slurry comprising acetone, dibutyl phthalate, silanized fumed $SiO_2$, and the VDF/HFP copolymer on a suitable substrate or carrier web and allowing the acetone to evaporate. No curing by radiation is required. The $SiO_2$ is a filler which imparts toughness and strength to the film. In addition, it is believed that the $SiO_2$ assists the activation process by creating physico-chemical conditions such that the electrolyte solution quickly and completely fills the pores created by the extraction of the dibutyl phthalate. Preferably, the polymeric slurry is mixed under low shear conditions as not to degrade the copolymer.

Preferably in preparing the polymer mixture for both the anode and cathode slurries is that the polymer (or copolymer) not be subject to high shear so as to be degraded. Furthermore, preferably the polymer or copolymer employed has a high average molecular weight. Preferably the average molecular weight is between 50K to 750K, more preferably 50K to 200K, and most preferably 50K to 120K. Furthermore, it is preferred that polymer or copolymer has a narrow molecular weight have range. Preferably the ratio of $M_n$ to $M_w$ is equal to about 1.

Next the dibutyl phthalate plasticizer is extracted from the precursor. Extraction can be accomplished using conventional organic liquid solvents such as diethyl ether or by a dense fluid or gas which refers to a gas compressed and heated to either supercritical or subcritical conditions to achieve liquid-like densities. Dense gases and fluids are known in the art. See, for example, U.S. Pat. Nos. 5,013,366, 5,267,455, 4,219,333, 4,012,194, and 3,969,196, which are incorporated herein. A preferred dense gas is carbon dioxide. The precursor is than pre-packaged in moisture-impermeable material which is described, for example, in U.S. Pat. No. 5,326,653 which is incorporated herein, before being activated. Activation with the inventive solvent which comprises a mixture of DIPC and EC (1:1 wt %) and lithium salt preferably occurs in an inert (e.g., argon) atmosphere. Finally, the packaging of the electrochemical cell is sealed.

While the invention has been described in terms of various preferred embodiments, the skilled artisan will appreciate the various modifications, substitutions, and changes which may be made without departing from the spirit hereof. The descriptions of the subject matter in this disclosure are illustrative of the invention and are not intended to be construed as limitations upon the scope of the invention.

What is claimed is:

1. An electrochemical cell comprising:
    an anode comprising a carbon anode active material comprising graphite, coke, or mixtures thereof, and a binder;
    a cathode; and
    an electrolyte, that is interposed between the anode and cathode, that comprises a polymeric matrix, a salt and a solvent comprising a carbonate having the structure R'OCOOR" where R' and R" are independently selected from branched alkyl groups with 3 to 7 carbons.

2. The electrochemical cell of claim 1 characterized by a first cycle capacity loss of less than about 15 percent and said anode further characterized by a reversible capacity of greater than about 316 mAh/g.

3. The electrochemical cell of claim 1 wherein the solvent has a melting point of less than about −30° C.

4. The electrochemical cell of claim 1 wherein the solvent is a mixture comprising diisopropyl carbonate.

5. The electrochemical cell of claim 1 wherein the solvent is a mixture comprising diisopropyl carbonate (DIPC) and a second solvent that is selected from the group consisting of ethylene carbonate, dimethyl carbonate, diethyl carbonate, dipropyl carbonate, dibutyl carbonate, diethoxy ethane, ethyl methyl carbonate, butylene carbonate and mixtures thereof wherein the weight ratio of DIPC to said second solvent is about 1:9 to 9:1.

6. The electrochemical cell of claim 1 wherein said salt comprises $LiPF_6$.

7. The electrochemical cell of claim 1 wherein the carbon anode active material is graphite.

8. The electrochemical cell of claim 7 wherein the cathode comprises a cathode-active material that is selected from the group consisting of $LiMn_2O_4$, $LiCoO_2$, $LiNiO_2$, and mixtures thereof.

9. A method of fabricating an electrochemical cell comprising the steps of:
    (a) providing an anode comprising graphite, coke, or mixtures thereof, and a binder;
    (b) providing a cathode; and
    (c) forming an electrolyte containing a polymeric matrix, a salt and a solvent mixture that is interposed between said anode and said cathode wherein the solvent comprises a carbonate having the structure R'OCOOR" where R' and R" are independently selected from branched alkyl groups with 3 to 7 carbons.

10. The method of claim 9 wherein the cell is characterized by a first cycle capacity loss of less than about 15 percent and said anode further characterized by a reversible capacity of greater than about 316 mAh/g.

11. The method of claim 9 wherein the solvent has a melting point of less than about −30° C.

12. The method of claim 9 wherein the solvent is a mixture comprising diisopropyl carbonate.

13. The method of claim 9 wherein the solvent is a mixture comprising diisopropyl carbonate (DIPC) and a second solvent selected from the group consisting of ethylene carbonate, dimethyl carbonate, diethyl carbonate, dipropyl carbonate, dibutyl carbonate, diethoxy ethane, ethyl methyl carbonate, butylene carbonate and mixtures thereof wherein the weight ratio of DIPC to said second solvent is about 1:9 to 9:1.

14. The method of claim 9 wherein said salt comprises $LiPF_6$.

15. The method of claim 9 wherein the carbon anode active material is graphite.

16. The method of claim 15 wherein the cathode comprises a cathode-active material that is selected from the group consisting of $LiMn_2O_4$, $LiCoO_2$, $LiNiO_2$, and mixtures thereof.

17. A method for reducing the decomposition of a solvent mixture comprising linear dialkyl carbonate and for reducing the formation of gaseous constituents in an electrochemical cell that includes an electrolyte, which comprises a polymeric matrix a salt and the solvent mixture, that is interposed between an anode and cathode, said method comprising adding a non-linear, branched alkyl group comprising a carbonate having the structure R'OCOOR" where R' and R" are independently selected from branched alkyl groups with 3 to 7 carbons, to said solvent mixture, said carbonate characterized by lesser rate of gas formation during cycling of said cell as compared to said linear dialkyl carbonate.

18. The method according to claim 17 wherein the carbonate added is diisopropyl carbonate.

19. An electrochemical cell comprising:
    an anode comprising a carbon anode active material comprising graphite, coke, or mixtures thereof, and a binder;
    a cathode; and
    an electrolyte, that is interposed between the anode and cathode, that comprises a salt and a solvent wherein the solvent consists essentially of one or more carbonates wherein each carbonate has the structure R'OCOOR" where R' and R" are independently selected from branched alkyl groups with 3 to 7 carbons.

20. The electrochemical cell of claim 19 characterized by a first cycle capacity loss of less than about 15 percent and said anode further characterized by a reversible capacity of greater than about 316 mAh/g.

21. The electrochemical cell of claim 19 wherein the solvent has a melting point of less than about −30° C.

22. The electrochemical cell of claim 19 wherein the solvent is diisopropyl carbonate.

23. The electrochemical cell of claim 19 wherein the electrolyte further comprises a polymeric matrix.

24. The electrochemical cell of claim 19 wherein said salt comprises $LiPF_6$.

25. The electrochemical cell of claim 19 wherein the carbon anode active material is graphite.

26. The electrochemical cell of claim 25 wherein the cathode comprises a cathode-active material that is selected from the group consisting of $LiMn_2O_4$, $LiCoO_2$, $LiNiO_2$, and mixtures thereof.

* * * * *